United States Patent [19]

Calamur et al.

[11] 4,296,637
[45] Oct. 27, 1981

[54] METHOD AND APPARATUS FOR SAMPLING HOT HOMOGENEOUS MIXTURES

[75] Inventors: Narasimhan Calamur; Morris R. Schoenberg, both of Naperville, Ill.

[73] Assignee: Standard Oil Company (Indiana), Chicago, Ill.

[21] Appl. No.: 134,879

[22] Filed: Mar. 28, 1980

[51] Int. Cl.³ .......................... G01N 1/22; H05B 3/06
[52] U.S. Cl. .............................. 73/863.11; 73/864.91; 219/312; 219/386
[58] Field of Search .......... 73/421 R, 422 R, 421.5 R; 422/102; 219/385, 386, 521, 310, 312

[56] References Cited

U.S. PATENT DOCUMENTS

| | | | |
|---|---|---|---|
| 1,942,382 | 1/1934 | Britton | 219/385 |
| 2,380,977 | 8/1945 | Lewis | 73/421.5 R |
| 3,338,087 | 8/1967 | Moberg et al. | 73/421.5 R |
| 3,487,692 | 1/1970 | Cook, Jr. | 73/421.5 R |

Primary Examiner—S. Clement Swisher
Attorney, Agent, or Firm—David E. Boone; William H. Magidson; William T. McClain

[57] ABSTRACT

A portable vessel for a sample of gas, some components of which may condence when cooled to ambient temperature. The container with inlet and outlet valves is surrounded by a heater and insulation so that the sampled material can be maintained above the dew point of any of its components.

A method of use includes the step of purging the vessel with inert gas prior to the sample collection and introduction of the sample into an analyzer.

9 Claims, 4 Drawing Figures

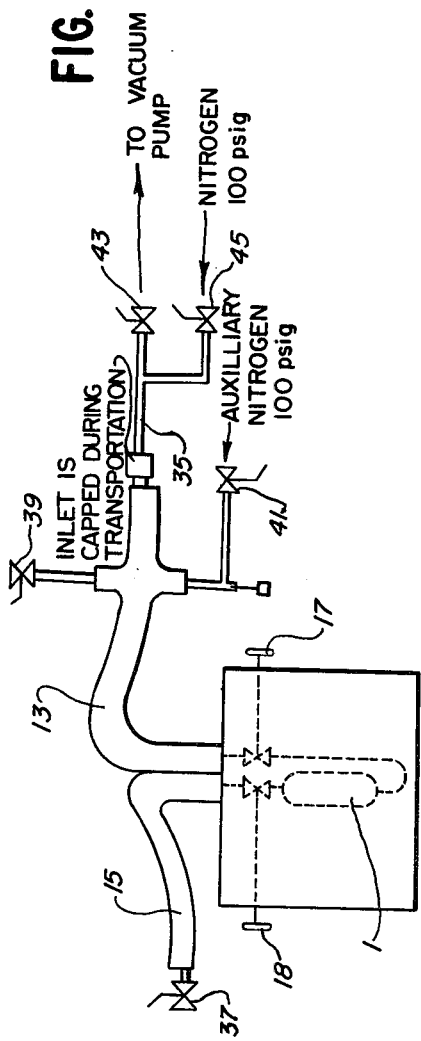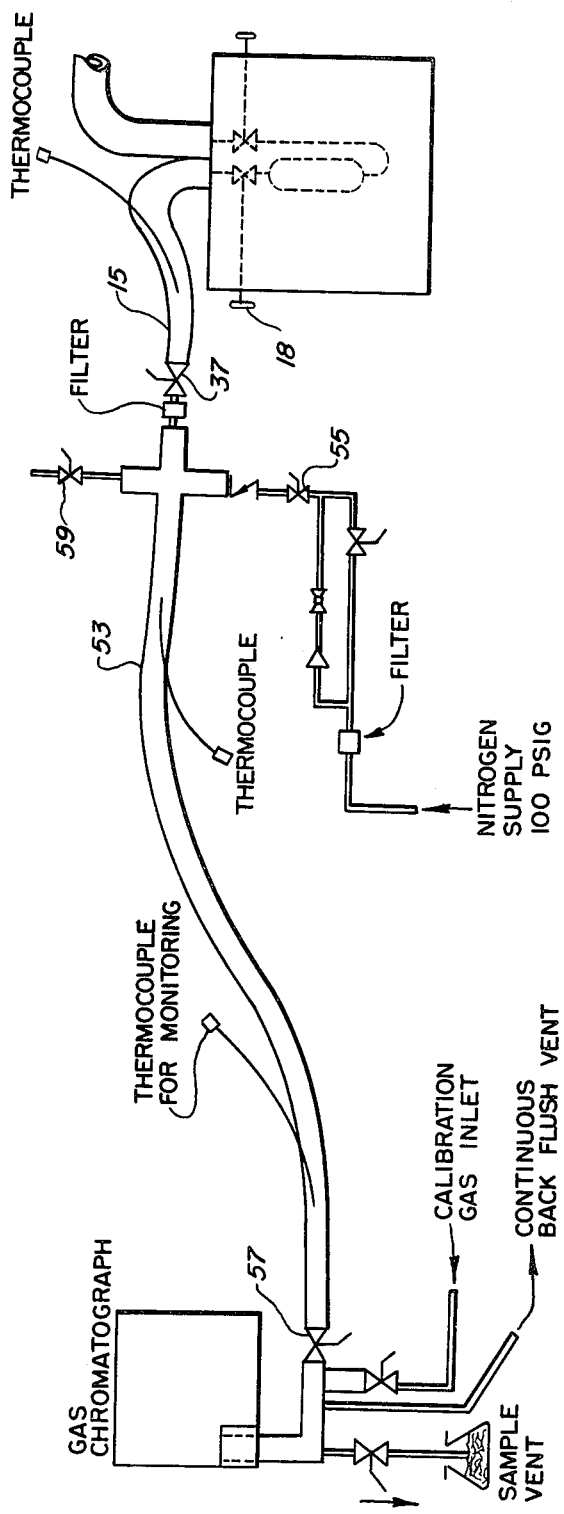

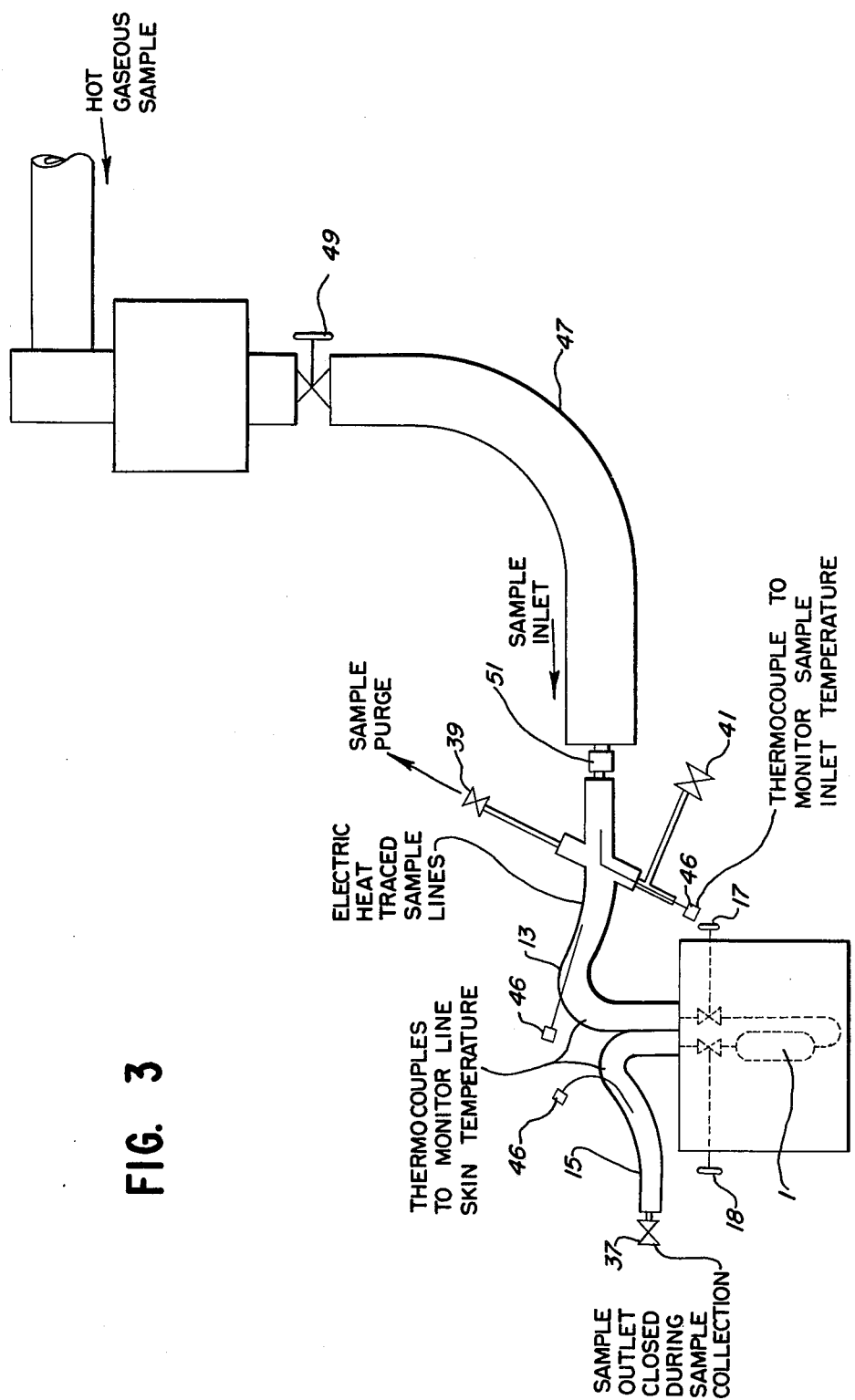

METHOD AND APPARATUS FOR SAMPLING HOT HOMOGENEOUS MIXTURES

This invention relates to the method and apparatus for sampling hot homogeneous mixtures which form multiple phases when cooled and more particularly to the portable apparatus and method for the periodic sampling of hot mixtures which form multiple phases at ambient temperatures.

In order to monitor and control a chemical process, it is generally desirable to obtain a total analysis of the process stream. There are many chemical process streams which are gaseous under processing conditions but form multiple phases at lower temperatures, for example, the streams formed in the thermal or catalytic cracking of hydrocarbons, vapor phase alkylation processes, and the oxidation of xylenes to aromatic acids. Ordinarily as a sample from such a process stream cools, the dew point(s) of certain components is reached and these components condense to form one or more liquid phases in which a portion of the remaining gaseous component(s) can be dissolved. Total analysis of such a multiphased sample is difficult and can be particularly time consuming and inaccurate when, for example, a portion of a gaseous component dissolves in a liquid phase. Other difficulties are pointed out below.

Several methods and apparatus for obtaining samples of gaseous mixtures have been described in the prior art. One method for obtaining a composite sample of a gas stream over a period of time is disclosed by Price et al in U.S. Pat. No. 3,429,186. This apparatus is suitable for samples which remain homogeneous and do not contain any condensable fractions.

A common method of analyzing samples which contain gaseous and liquid phases is described by Himes et al in U.S. Pat. No. 3,956,921 which involves separating the mixture into condensate (liquid) and liquid-free gaseous components and analyzing each. This procedure has several disadvantages which affect the accuracy of the results including:

(a) the long time required to collect a sufficient quantity of the liquid fraction if the liquid is a minor component;
(b) the distribution of some components between liquid and gaseous fractions;
(c) the mechanical handling problems with the liquid phase such as liquid hang up on container walls; and,
(d) the formation of an emulsion in the liquid phase.

A method and apparatus for sampling refrigerated mixtures of volatile liquids are disclosed by Cook in U.S. Pat. No. 3,487,692. A sample of the refrigerated mixture is passed into an insulated, pre-cooled sample container and then warmed at constant volume while maintaining the pressure greater than the cricondenbar of the mixture by use of a relief valve. The pressures involved with such a system are usually very high.

A nonportable device for sampling hot gaseous mixtures containing easily condensable components is disclosed by Granger et al in U.S. Pat. No. 3,517,557. This device is permanently attached to the plant line from which the sample is to be drawn with a sampling tube leading from the plant line to a sampling valve within a heated housing. The sampling valve entrains the sampled gas with an inert gas and transmits the mixture to a chromatograph for analysis. The temperature within the housing is maintained at at least 150° C. by a heater to keep the sampled gas at a temperature above the condensing temperature of the condensable components of the sample. This procedure has the disadvantage of requiring a gas chromatograph in close proximity to the sampling device which adds greatly to the expense of the sampling procedure since a special plant site installation would be required to house the gas chromatograph instruments as they are neither rugged nor explosion-proof.

Consequently there is a need for a portable apparatus and method for sampling hot gaseous mixtures which allows the periodic taking of samples at various places in a plant and the transportation of the samples to analytical instruments for analysis while maintaining the sample as a homogeneous mixture.

Accordingly an object of the present invention is to provide a portable hot gas sampler apparatus and method by which samples of homogeneous hot gaseous mixtures can be taken, transported to, and introduced into analytical instruments. Other objects appear hereinafter.

The present invention in one of its embodiments is a portable apparatus for sampling hot homogeneous gaseous mixtures which form multiple phases at ambient temperatures. The apparatus comprises a sample vessel for holding the sample mixture, sample inlet and outlet means attached to said vessel, valve means located in said inlet and outlet means, a heating means positioned around said vessel and said valve means to provide a heated zone which contains said vessel and said valve means, insulating means surrounding said vessel and said heating means, an outer housing which encloses said insulating means and through which said inlet and outlet means passes.

Another embodiment of the present invention is a method of collecting a sample of a hot homogeneous gaseous mixture which forms multiple phases at ambient temperatures.

The method comprises heating a sample vessel and attached inlet and outlet means containing the valve means to a temperature sufficiently above the dew point of the sample mixture to maintain the sample as a homogeneous mixture. The sample vessel, inlet and outlet means and valve means are purged of contaminants. Hot sample mixture is then used to purge the sample line and valve to eliminate any cold spots. A portion of the homogeneous mixture is then collected in said sample vessel and the vessel is sealed with the valve means. The sample vessel containing the sample portion is then transported to the analytical means and the sample is analyzed before the sample mixture can cool to the dew point of the mixture.

Further objects and advantages of the present invention will become apparent when the following description is read in connection with the accompanying drawing.

FIG. 2 is a schematic diagram showing a purging set up for a hot gas sampler apparatus.

FIG. 3 is a schematic diagram showing a set up and illustrating a procedure for collecting a sample in a hot gas sampler appartus.

FIG. 4 is a schematic diagram showing a set up for supplying aliquots of sample to a gas chromatograph from a hot gas sampler apparatus.

Figure 1:
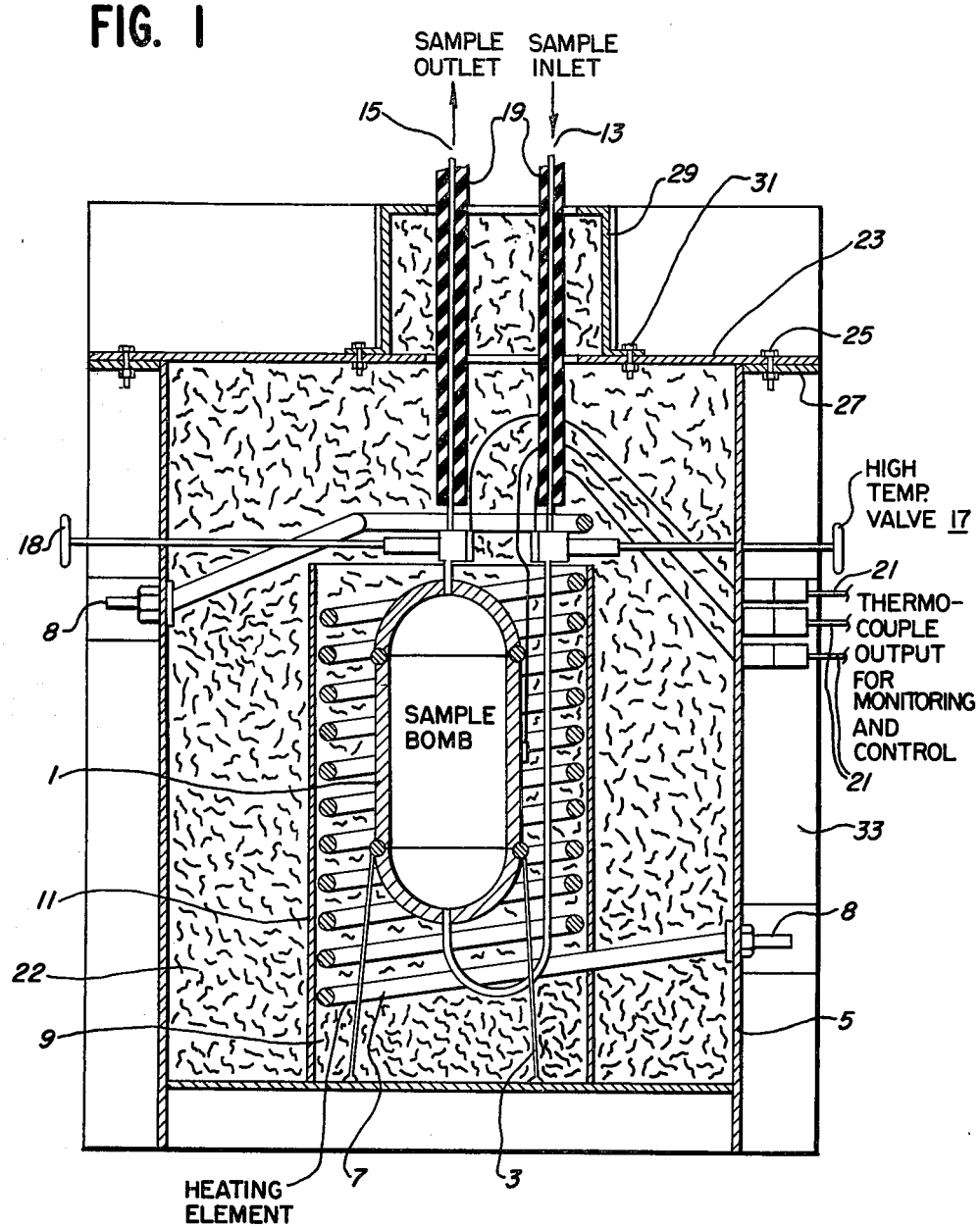
FIG. 1 is a sectional view of a specific embodiment of the hot gas sampler apparatus of this invention.

The method and apparatus of the present invention are adapted for use with any mixture of materials whose dew point is between ambient temperature and the process temperature. Ambient temperature is used herein to mean the temperature of the atmosphere which surrounds the sampler apparatus. The process temperature is the temperature of the process stream being sampled. Dew point is used herein to mean the temperature at which one or more components of a gaseous mixture begin to condense. Consequently, the present invention is useful for any mixture which is single-phased under process conditions but becomes multiphased when cooled to a temperature below the process temperature but above ambient temperature. The instant invention is particularly useful for collecting samples from the process streams in plants where hydrocarbons are thermally or catalytically cracked or reformed as in plants for the production of olefins such as ethylene and propylene.

A first embodiment of apparatus for carrying out the sampling method of the instant invention is shown in FIG. 1. Sample vessel 1 is a vessel capable of withstanding the particular temperature and pressure of the process stream to be sampled. For example, if a process stream in a plant for the thermal cracking of hydrocarbons were sampled, sample vessel 1 would ordinarily be exposed to a mixture with temperature in excess of 400° F. and a pressure of less than 50 psig. The internal surface of the vessel 1 should be chemically and physically inert to the sample in the temperature range in which the sample would be stored i.e., ordinarily a temperature range from the dew point up to the temperature of the process stream from which the sample is taken. By chemically inert is meant that the vessel 1 should be of a material or be treated to minimize surface catalyzed reactions which occur particularly at high temperatures and can result in erroneous analyses. By physically inert is meant that trace components of the mixture should not be adsorbed on the surface of the vessel 1. Consequently, surface coatings such as poly(tetrafluroethylene) are not suitable since trace components could be adsorbed. A preferred material is stainless steel which has been surface coated with aluminum to minimize surface catalyzed reactions. The vessel 1 must be of sufficient size to provide a large enough sample for analysis; however, the size of the vessel is limited by the requirement that the sampler apparatus be portable. We have found that a 500-milliliter, high-pressure, stainless steel vessel whose interior surface has been coated with aluminum meets these requirements.

The sample vessel 1 is supported by supports 3 which are attached to the vessel 1 and to the bottom of housing 5. Preferably these supports are steel rods which are welded to vessel 1 and housing 5.

A heater 7 surrounds the sample vessel 1 and provides a heated zone inside of which all metal surfaces in contact with the stored sample are located to prevent local cold spots. The heater can be any device which can provide controllable temperatures in excess of the dew point of the sample mixture. Preferably the heater should be capable of providing temperatures in excess of 800° F. For ease of connection and control electrical resistance heaters are preferred. This type of heater is shown in the apparatus in FIG. 1 with leads 8 for connecting the electrical source. While the heater 7 can be in direct contact with the sample vessel 1, we have found that hot spots can occur which can cause changes in the sample composition. Therefore, it is preferred as shown in FIG. 1 that the heater 7 not be in direct contact with the vessel 1. The space between the heater 7 and vessel 1 is preferably filled with packing 9 which will decrease the radiant heat transferred from the heater 7 to vessel 1 to minimize temperature overshoot as the vessel is heated since as discussed hereinbelow the heater 7 is controlled by a sensor attached to the surface of vessel 1. Packing 9 can be any material normally used in a packed heater, for example, sand or steel balls. However, since packing 9 should be a light weight material to minimize the weight of the sampler apparatus, aluminum oxide balls with a diameter of about ¼ inch are preferred. The vessel 1 and heater 7 can be surrounded by an inner container 11 which is attached to housing 5 at the bottom and is open at the top. This inner container 11 allows the packing 9 to fill the space between vessel 1 and heater 7. Inner container 11 is formed from any material which will withstand the high temperatures of heater 7. For example, stainless steel sheet with a thickness of about 0.0375 inch is used.

The sample mixture enters sample vessel 1 through a sample inlet means such as line 13. While line 13 can also be used as a sample outlet means, it is preferred that a separate sample outlet line 15 be utilized as shown in FIG. 1. The use of two lines allows the sample vessel 1 and associated lines to be more easily cleaned with solvents such as benzene or toluene. Also the presence of two or more lines to the vessel 1 allows the lines and vessel 1 to be readily flushed with the sample stream as discussed hereinbelow.

Each sample line is equipped with a high temperature valve means such as valve 17 for the inlet line and 18 for the outlet line which seal vessel 1 when it contains a hot sample at the operating pressure. An example of a suitable valve is a Nupro valve. To avoid unnecessary maintenance, the valve should be located so that the packing portion of the valve is outside the hot zone described hereinabove while the main body of the valve is inside the zone and heated to avoid any cold spots where any sample component might condense. Those portions of sample lines 13 and 15 which communicate between sample vessel 1 and valves 17 and 18 are surrounded by heater 7 and are within the hereinabove described heating zone. Those portions of sample lines 13 and 15 which run from valves 17 and 18 to outside the hot gas sampler are heat traced 19 to eliminate cold spots. Preferably electrical heating tape is used as heat tracing 19.

The temperatures of sample vessel 1 and valves 17 and 18 are monitored by sensors 21. The sensor on the sample vessel 1 is used in conjunction with a controller such as a Eurotherm 101 to control heater 7. The sensors 21 can be any type used by those skilled in the art for the temperature range which would be encountered for a particular sample, for example, Type J thermocouples.

The insulating means 22 must be of sufficient efficiency and thickness to maintain the temperature of the sample mixture above its dew point. Accordingly, the insulation must be of sufficient efficiency to maintain the vessel 1 and valves 17 and 18 at a temperature above the dew point of any component in the sample for several hours without heat input to allow the sample mixture to be transported from the sampling point to the analytical instrument and conduct the analysis. For most samples it is sufficient if the temperature loss of the sample is less than about 20° F. per hour at a sample temperature of 400° F. However, if there is a narrow temperature range between the dew point and the temperature stability limit of the sample (temperature at which thermally induced reactions such as hydrogenation occur), then a temperature loss of 20° F. per hour might be too great if the sample cannot be immediately analyzed. In such a case, the amount of insulation can be increased to minimize the heat loss. Therefore, the material chosen for insulation 22 should have low bulk density preferably less than about 10 pounds per cubic foot and low thermal conductivity preferably less than about 0.6 BTU/hr./ ft$^2$/inch/° F. A material which has been found suitable for use in Corborendum Fiberfrax ® bulk fiber. We found this material worked well when packed at a density of about 8 pounds per cubic foot between inner container 11 and housing 5 and a density of about 2 pounds per cubic foot around valves 17 and 18. If the insulation around these valves is more densely packed then about 2 pounds per cubic foot, there is insufficient heat supplied from the "heat sink" which includes vessel 1 and packing 9 and a cold spot can occur in the valve body causing condensation of sample components.

Housing 5 is necessary to provide structural support for the sample vessel 1, heater 7, and the rest of the apparatus. The housing 5 can be constructed from any material which has the required structural integrity and can withstand high temperatures. Stainless steel sheet of about 0.062 inch thickness is preferred.

After housing 5 has been packed with insulation 22, top lid 23 is bolted into place using bolts 25 which are attached to flange 27. Top lid 23 contains a hole of sufficient size to allow passage therethrough of lines 13 and 15. Over said hole is positioned a cap 29 which is filled with insulation 22. Said cap 29 is bolted into place using bolts 31. Cap 29 also contains a hole of sufficient size to allow passage therethrough of lines 13 and 15.

Since housing 5 can become very hot in spite of insulation 22, additional insulation 33 is attached to the outside of housing 5 for safety in handling and to further minimize heat loss. While any material with the necessary insulating properties, structural integrity and thermal stability can be used, black polystyrene foam which is capable of withstanding temperatures up to about 250° F. in a thickness of about one inch has been found to be particularly effective.

The hot gas sampler including its inlet and outlet lines 13 and 15 and auxiliary controls can be mounted in a portable cabinet for more convenient use at a sample collection site. The auxiliary controls include a controller and voltage regulator for controlling the heat input to the sample vessel 1 and the inlet and outlet lines 13 and 15.

In a preferred operation of the hot gas sampler apparatus as shown in FIG. 2, a vacuum/inert gas purging set up 35 is connected to inlet line 13. A slow purge of the inert gas, preferably nitrogen, is maintained through the sample vessel 1 and inlet and outlet lines 13 and 15 while said vessel and lines are heated to a temperature above the dew point of the sample to be collected and preferably at least about 20° F. above the dew point. For convenience this operation is ordinarily carried out in the plant laboratory. Once a steady state temperature has been reached in vessel 1 and lines 13 and 15, said vessel and lines are purged, preferably by repeatedly evacuating and pressurizing with nitrogen, to remove traces of contaminants. In this operation valves 37, 39 and 41 are closed while valves 17, 18 and 43 are open to evacuate said vessel and lines to about 4 psia (pounds per square inch absolute); then valve 43 is closed and valve 45 is opened to admit nitrogen at 100 psig (pounds per square inch gauge). This process is repeated ten times to ensure removal of all contaminants in the sampler system. Valve 43 is then closed and valve 45 is opened to pressurize the sample system, i.e., vessel 1 and lines 13 and 15, to 100 psig with nitrogen; then valve 18 is closed. Vessel 1 and line 13 are then pressured and evacuated ten times following the procedure described hereinabove. Valve 17 is then closed to isolate evacuated vessel 1 at 4 psia. Line 13 is purged by opening valve 41 while purge set up 35 is disconnected and line 13 is then capped.

Line 13 is then pressured to 100 psig through valve 41 which is then closed and disconnected from the nitrogen source. The hot gas sampler apparatus is now ready to be moved to the sample collection point. The above described series of operations prevents air from entering the evacuated sampler vessel 1 while it is being transported to the sample collection site. Of course, if it is more convenient, the heating and purging operation can be conducted at the sample collection site.

In order to collect a sample from a process stream which is at a relatively low pressure, for example, less than 50 psig, it is preferred that the sample be conveyed into an evacuated sample vessel 1. Collecting the sample in an evacuated vessel 1 maximizes the quantity of sample obtained at the low process pressure without extended flushing of the vessel 1 with sample mixture. If the process stream is at a high pressure, then sufficient sample can be collected even though vessel 1 contains one atmosphere of nitrogen. Even so the generally preferred method of operation is to collect the sample in an evacuated vessel 1 as described hereinabove.

For purposes of illustration, the method of collecting a sample from a process stream in a plant for the thermal cracking of hydrocarbons to form olefins such as ethylene and propylene is described hereinbelow. Similar procedure and apparatus would be utilized for the collection of a sample from any gaseous process stream. A sample from such a thermal cracking process stream ordinarily contains about 23 to 39 eight percent water, about 14 to 18 weight percent hydrocarbons condensable at room temperature and 47 to 58 weight percent gaseous components. The dew point of such a sample ordinarily ranges from about 320° to 340° F.

Once the sampler apparatus is at the sample collection site as shown in FIG. 3, the inlet and outlet lines 13 and 15 are electrically heated to maintain the temperature of said lines at least about 20° F. above the dew point of the sample to be collected in this example 400° to 410° F. The temperatures are monitored using sensors such as thermocouples 46. A nitrogen purge is attached to valve 41 and the line 13 is uncapped and attached to a sample line 47 which is heated to about 400° F. Sample line 47 can be heated by any convenient means such as electrical or steam tracing although for most plant operations steam tracing is preferred. Valve 41 is closed and valve 49 is then opened to allow the sample gas stream to pass through line 47 and out valve 39. This sample purging is typically continued for about 15 minutes to allow section 51 to reach steady state temperature. Section 51 is preferably not electrically heat traced because of the potential shock hazard which could result from electrically tracing this section at the sampling site. After steady state temperature has been achieved, valve 49 is closed and valve 41 is momentarily opened to admit 100 psig nitrogen to blow out any possible condensate in the purge line. Valve 39 is then closed after the nitrogen pressure decays to ambient. Valve 49 is then opened followed by valve 17 to collect the sample in vessel 1. Once steady state pressure of about 7 psig is achieved, valve 17 is closed followed by valve 49 and the sample line is disconnected with nitrogen purge through valve 41. Sample inlet line 13 is capped and the hot gas sampler apparatus containing the sample is transported to the analysis site.

While the analysis of the sample can be carried out by any means suitable for the particular components of a sample such as infrared spectrometry, gas chromatography is generally the most useful method. FIG. 4 shows a sample injection system which has been found to be useful for the transmission of samples from the sample vessel 1 to a gas chromatograph. The sample injection lines 53 are maintained at a temperature at least 20° F. above the dew point of the sample and are constantly purged with nitrogen at 4 psig when not in use. Periodically, 100 psig nitrogen is blasted through lines 53 to make sure these lines are not blocked. Preferably the length of these sample injection lines should be as short as possible to minimize the dead volume in the system and hence the amount of sample which is required to obtain an analysis. To inject a sample, the nitrogen flow through lines 53 is stopped by closing valves 55 and 57. Valve 59 is opened and lines 53 and 15 are evacuated to about 4 psia. Valve 37 is momentarily opened to release the nitrogen pressure in outlet line 15. Valve 59 is closed and valve 18 is opened to allow gaseous sample from vessel 1 to pass into outlet line 15. Valves 37 and 57 are opened and the sample gas is allowed to purge the lines for 10 seconds before valve 57 is closed and a portion of the sample is injected into the gas chromatograph. Depending on the constituents of the sample it may be desirable to utilize more than one gas chromatograph with each instrument analyzing particular constituents of the sample. In this manner a total analysis of the gaseous sample can be obtained by integrating the eluting peak areas of the various components.

To determine if changes in sample composition occurred, a mixture with a dew point of about 330° F. was stored in a hot gas sampler apparatus as exemplified in FIG. 1. The sample vessel 1 was a 500-milliliter, stainless steel vessel whose inner surface had been aluminum coated ("Alonized") by Alon Processing, Inc. to minimize surface catalyzed reactions. The sample consisted of a mixture of hydrogen and various saturated and unsaturated hydrocarbons of up to four carbons. The components and the results are given in Table I. The components were analyzed on a Hewlett-Packard model 5840 gas chromatograph and values given are normalized percent area under peaks. These results show that there is little or no change in composition of the complex sample mixture when it is held at a temperature more than 100° F. above the dew point of the sample.

TABLE I

COMPOSITION COMPARISON: EFFECT OF HOLDING SAMPLE AT HIGH TEMPERATURES

| Components | Normalized % Area Under Peaks | | | |
|---|---|---|---|---|
| | Sample Held @ 550° F. | | Sample Held @ 435° F. | |
| | @ 0 Time | @ 1¼ Hour | @ 0 Time | @ 1 Hour |
| Hydrogen | 0.45 | 0.38 | 0.38 | 0.36 |
| Propane | 8.07 | 8.27 | 3.97 | 4.04 |
| Propylene | 10.24 | 10.30 | 7.68 | 7.68 |
| Acetylene | 0.79 | 0.29 | 1.21 | 1.19 |
| n-Butane | 0.16 | Negligible | 0.19 | 0.17 |

TABLE I-continued

COMPOSITION COMPARISON: EFFECT OF HOLDING SAMPLE AT HIGH TEMPERATURES

| Components | Normalized % Area Under Peaks | | | |
|---|---|---|---|---|
| | Sample Held @ 550° F. | | Sample Held @ 435° F. | |
| | @ 0 Time | @ 1¼ Hour | @ 0 Time | @ 1 Hour |
| i-Butylene | 0.53 | Negligible | 0.16 | 0.08 |
| 2-Butene Methyl acetylene | 0.21 | Negligible | 0.31 | 0.19 |
| 1,3-Butadiene | 1.82 | 1.59 | 2.13 | 2.05 |
| Methane | 27.91 | 28.09 | 29.16 | 29.30 |
| Ethylene | 46.81 | 47.58 | 51.56 | 51.83 |
| Ethane | 3.02 | 3.50 | 3.26 | 3.10 |

We claim:

1. A portable apparatus for sampling hot homogeneous mixtures which form multiple phases at a temperature above ambient temperature which comprises:
   (a) a sample vessel for holding a sample mixture;
   (b) sample inlet and outlet means attached to said vessel;
   (c) valve means located in said inlet and outlet means;
   (d) heating means positioned around said vessel, said valve means and that portion of said inlet and outlet means between said vessel and said valve means to provide a heated zone which contains said vessel, said valve means and said portion of said inlet and outlet means;
   (e) insulating means surrounding said vessel and said heating means; and
   (f) an outer housing which encloses said insulating means and through which said inlet and outlet means pass.

2. The apparatus of claim 1 wherein said heating means is adapted to heat said vessel above the dew point of said sample mixture.

3. The apparatus of claim 1 wherein said insulating means is adapted to maintain the temperature of said sample mixture above its dew point for a time sufficient to transport said apparatus from the sample collection site to the sample analysis location.

4. The apparatus of claim 1 adapted to be attached to a sample injection system of one or more gas chromatographs.

5. The apparatus of claim 1 wherein the inner surface of said sample vessel is chemically and physically inert to said sample mixture at temperatures from the dew point of the sample mixture up to at least the temperature of the mixture from which said sample is taken.

6. A portable apparatus for sampling hot homogeneous mixtures which form multiple phases at a temperature above ambient temperature which comprises:
   (a) a sample vessel for holding a sample mixture said vessel having an inner surface which is chemically and physically inert to said sample mixture at temperatures from the dew point of the sample mixture up to at least the temperature of the hot mixture from which said sample is taken;
   (b) sample inlet and outlet means attached to said vessel;
   (c) valve means located in said inlet and outlet means;
   (d) heating means adapted to heat said vessel above the dew point of said sample mixture positioned around said vessel, said valve means and that portion of said inlet and outlet means between said vessel and said valve means to provide a heated zone which contains said vessel, said valve means and said portion of said inlet and outlet means;

(e) insulating means surrounding said vessel and said heating means said insulating means adapted to maintain the temperature of said sample mixture above its dew point for a time sufficient to transport said apparatus from the sample collection site to the sample analysis location; and (f) an outer housing which encloses said insulating means and through which said inlet and outlet means pass.

7. A method for sampling hot homogeneous mixtures which form multiple phases at a temperature above ambient temperature which comprises:

(a) heating a sample vessel and attached inlet and outlet means and valve means to a temperature above the dew point of said homogeneous mixture;

(b) purging said sample vessel and said inlet and outlet means and valve means with an inert gas;

(c) collecting a portion of said hot homogeneous mixture in said sample vessel;

(d) sealing said sample vessel with said valve means; and (e) maintaining the temperature of said mixture above the dew point of said mixture.

8. The method of claim 7 comprising the additional step of injecting said hot homogeneous mixture into a sample injection system of one or more gas chromatographs.

9. The method of claim 7 wherein said hot homogeneous mixture comprises a process stream from a process for the thermal cracking of hydrocarbons.

* * * * *